United States Patent
Nagata et al.

(10) Patent No.: US 7,360,898 B2
(45) Date of Patent: Apr. 22, 2008

(54) EYE ACCOMMODATION FUNCTION STATE MEASUREMENT DEVICE AND EYE ACCOMMODATION FUNCTION STATE MEASUREMENT METHOD

(75) Inventors: Tatsuhiko Nagata, Tokyo (JP); Eishi Aizawa, Tokyo (JP); Tetsurou Nishida, Tokyo (JP)

(73) Assignee: Right Mfg. Co., Ltd., Tokyo (JP)

( * ) Notice: Subject to any disclaimer, the term of this patent is extended or adjusted under 35 U.S.C. 154(b) by 14 days.

(21) Appl. No.: 11/327,375

(22) Filed: Jan. 9, 2006

(65) Prior Publication Data

US 2006/0238708 A1 Oct. 26, 2006

(30) Foreign Application Priority Data

Jul. 9, 2003 (JP) ............... 2003-272295

(51) Int. Cl.
*A61B 3/10* (2006.01)
(52) U.S. Cl. .................................... 351/211
(58) Field of Classification Search ............ 351/205, 351/206, 208, 211–216
See application file for complete search history.

(56) References Cited

U.S. PATENT DOCUMENTS

2001/0026350 A1 * 10/2001 Fujieda ............... 351/212

FOREIGN PATENT DOCUMENTS

| JP | 06-165757 | 6/1994 |
|----|-----------|--------|
| JP | 06-165760 | 6/1994 |
| JP | 2003-070740 | 3/2003 |

* cited by examiner

*Primary Examiner*—Alicia M Harrington

(57) ABSTRACT

The present invention provides an eye accommodation function state measurement device which places only a small burden on the subject, allows confirmation of an intermediate measurement result, and is more conveniently used. The eye accommodation function state measurement device disposes an image at a plurality of positions by using an image moving mechanism, and measures the accommodation function state of the subject's eye at each position. The eye accommodation function state measurement device includes a control section (65) which provides a measurement suspension period (S6 to S10) in which the measurement is suspended. In the measurement suspension period, the eye accommodation function state measurement device calculates the eye accommodation function state (S7), displays the intermediate measurement result of the eye accommodation function state (S8), or transmits data from the control section (65) to an external storage section (69) (S9).

6 Claims, 6 Drawing Sheets

* # EYE ACCOMMODATION FUNCTION STATE MEASUREMENT DEVICE AND EYE ACCOMMODATION FUNCTION STATE MEASUREMENT METHOD

This application claims the benefit of PCT International Application Number PCT/JP2004/007199 filed May 20, 2004 and the corresponding Japanese Application, filed Jul. 9, 2003, in Japan, the disclosures of which are incorporated herein by reference.

TECHNICAL FIELD

The present invention relates to an eye refractive power measurement device which measures the refractive power of the subject's eye and the eye accommodation function state of the subject's eye.

BACKGROUND ART

In the field of medical treatment such as ophthalmology, eye accommodation function state measurement has been demanded. For example, a device which objectively measures the eye accommodation function has been proposed, such as an eye accommodation function state measurement device disclosed in patent document 1.

In eye accommodation function state measurement, according to the patent document 1, the eye's refractive power is continuously measured in the same manner as in a known refractive power measurement method (e.g. method disclosed in patent document 2), and high-frequency components of the refractive power are calculated from the measured refractive power values to determine the eye accommodation function state. The method disclosed in the patent document 1 requires continuous refractive power measurement for high-frequency components of 1 Hz to 2.3 Hz. When the frequency is set at 1 Hz, an eye refractive power measurement section continuously measures the refractive power at intervals of 0.1 sec, for example. The continuous measurement is performed for about 20 sec/cycle at a number of positions while moving the target position (e.g. about eight cycles at eight positions).

In related-art eye accommodation function state measurement, when performing 20-sec measurements in eight cycles, the measurement is performed for 160 seconds in total. Since the subject must continuously stare at the target during the measurement, the subject becomes tense when the measurement continues for such a long time.

Moreover, the subject suffers from continuously seeing the target for 160 seconds.

As refractive power measurement data, three kinds of data (i.e. spherical power data, cylinder power data, and astigmatic axis data) need to be stored. Therefore, when measuring the refractive power for 160 seconds at intervals of 0.1 second, 4800 pieces of data in total must be stored. This poses a problem in which a storage section must have a high capacity.

Moreover, since the measurement results can be obtained after measuring the refractive power for 160 seconds, even if data necessary for calculating the eye accommodation function state is insufficient due to movement of the eye, occurrence of a number of blinks, or the like, the operator continues the measurement operation without knowing such a data insufficiency. Therefore, if a measurement error has occurred, the measurement must be carried out again from the start.

(Patent document 1) JP-A-2003-70740
(Patent document 2) JP-A-6-165757

DISCLOSURE OF THE INVENTION

An objective of the present invention is to provide an eye accommodation function state measurement device which places only a small burden on the subject, allows confirmation of an intermediate measurement result, and is more conveniently used.

The present invention achieves the above objective by providing the following solution means. The following means is described using symbols corresponding to those used in embodiments of the present invention so that the present invention is readily understood. However, the present invention is not limited thereto.

A first invention provides an eye accommodation function state measurement device (51) comprising: an image projection section (62) which projects an image (62a) onto a subject's eye; and an image moving mechanism which moves a position of the image along a direction of an optical axis of the subject's eye; the eye accommodation function state measurement device disposing the image at a plurality of positions by using the image moving mechanism, and measuring an accommodation function state of the subject's eye at each position; the eye accommodation function state measurement device further comprising a control section (65) which provides a measurement suspension period in which the measurement is suspended (S6 to S10).

A second invention provides the eye accommodation function state measurement device (51) according to the first invention, wherein the control section (65) calculates the eye accommodation function state within the measurement suspension period (S7).

A third invention provides the eye accommodation function state measurement device (51) according to the first invention, wherein an intermediate measurement result of the eye accommodation function state is displayed within the measurement suspension period (S8).

A fourth invention provides the eye accommodation function state measurement device (51) according to the first invention, comprising a measurement suspension notification section (S6) which indicates start and/or completion of the measurement suspension by using a display and/or voice.

A fifth invention provides the eye accommodation function state measurement device (51) according to the first invention, comprising a remeasurement select section (68, S11) which allows selection of remeasurement without moving the position of the image in the measurement suspension period.

A sixth invention provides the eye accommodation function state measurement device (51) according to the first invention, wherein the control section transmits data to an external storage section (69) in the measurement suspension period (S9).

A seventh invention provides an eye accommodation function state measurement device (51) comprising: an image projection section (62) which projects an image (62a) onto a subject's eye; and an image moving mechanism which moves a position of the image along a direction of an optical axis of the subject's eye; the eye accommodation function state measurement device disposing the image at a plurality of positions by using the image moving mechanism, measuring an accommodation function state of the subject's eye at each position, and displaying at least one of positional information of the image and measurement time information at least in the middle of the measurement (S3).

An eighth invention provides an eye accommodation function state measurement method comprising: moving a position of an image (62a) projected onto a subject's eye along a direction of an optical axis of the subject's eye to dispose the image at a plurality of positions; measuring an accommodation function state of the subject's eye at each position; and suspending the measurement before completing all the measurements.

According to the present invention, since the measurement suspension period is provided in the middle of the measurement operation, the subject need not endure a long measurement time and is not unnecessarily subjected to tension. Moreover, since the operator can check the intermediate measurement result, the operator can find a measurement error in the middle of the measurement, so that the measurement can be performed without unnecessarily increasing the measurement time. Since the device according to the present invention processes data in the measurement suspension period, it is unnecessary to use a high-speed CPU, so that an inexpensive device can be provided. Moreover, since it is unnecessary to provide a high-capacity memory by outputting the measurement data to the external device in the middle of the measurement, an inexpensive device can be provided.

As described above, according to the present invention, an eye accommodation function state measurement device and method which place little burden on the subject and the operator, exhibit excellent operability, and are inexpensive, can be provided.

BRIEF DESCRIPTION OF THE DRAWINGS

FIG. 2 is a diagram showing a striped pattern of a chopper 61a.

BEST MODE FOR CARRYING OUT THE INVENTION

The present invention achieves the objective of providing an eye accommodation function state measurement device and method which place little burden on the subject and the operator, exhibit excellent operability, and are inexpensive by providing a measurement suspension period.

Embodiments of the present invention are described below with reference to the drawings.

Figure 1:
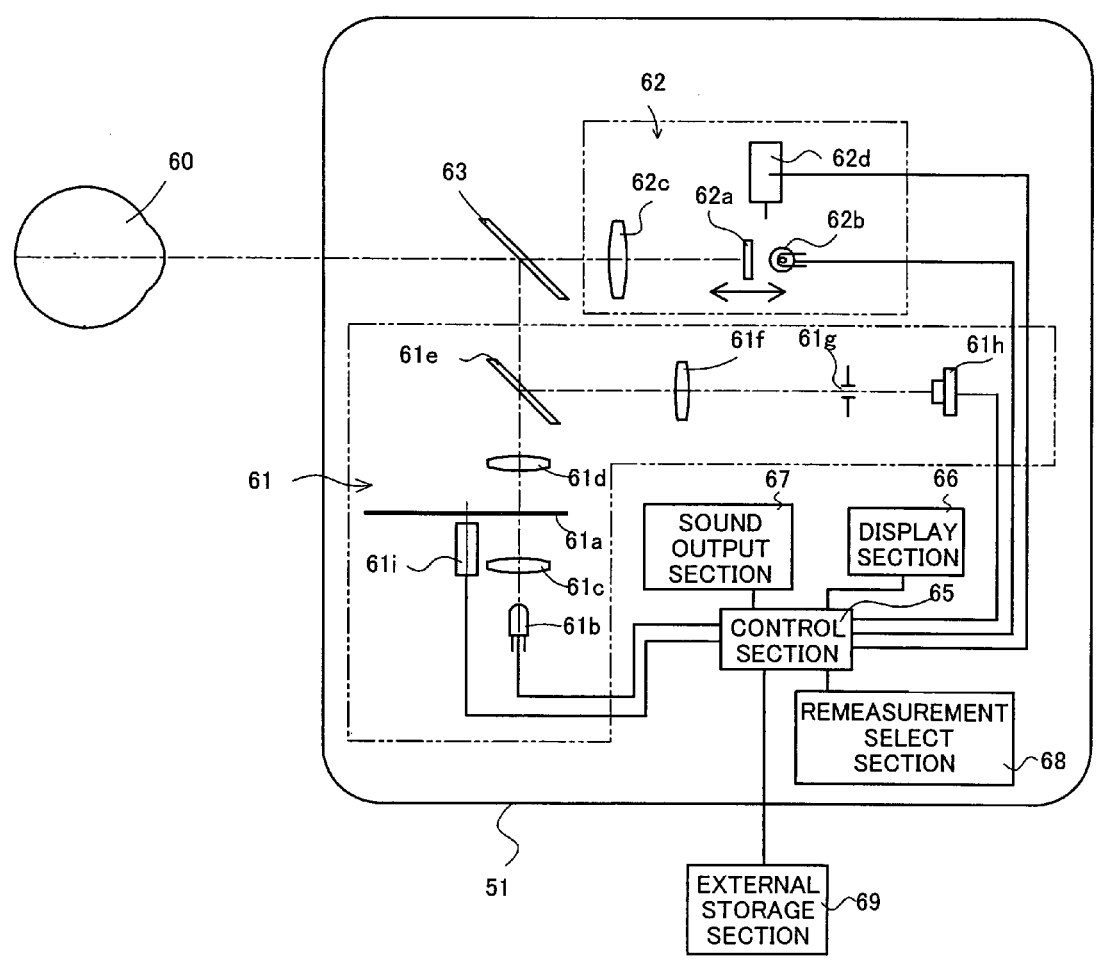
FIG. 1 is a configuration diagram of an eye accommodation function state measurement device 51 according to one embodiment of the present invention.

FIG. 1 is a configuration diagram of an eye accommodation function state measurement device 51 according to one embodiment of the present invention. The configuration of the device used in the present invention is similar to those of the devices disclosed in the patent documents 1 and 2. The device used in the present invention utilizes retinoscopy as the measurement principle. The basic principle of obtaining one refraction measurement value is similar to that disclosed in the patent documents 1 and 2. Therefore, details of the measurement principle are omitted.

As shown in FIG. 1, the eye accommodation function state measurement device 51 includes a refraction measurement section 61, an image projection section 62, a dichroic mirror 63, a control section 65, a display section 66, a sound output section 67, a remeasurement select section 68, and the like. An external storage section 69 for storing data is provided outside the eye accommodation function state measurement device 51.

In the projection section 62, a convex lens 62c, a target 62a, and a light source 62b are disposed from the side near the subject's eye 60. A luminous flux from the target 62a illuminated by the light source 62b is incident on the subject's eye 60 after being converted into a state similar to a parallel luminous flux by the convex lens 62c. Therefore, the target 62a is seen at a position farther than the actual position. The target 62a and the light source 62b can be moved by using a target moving mechanism (not shown) and a motor 62d in the direction of the optical axis of the subject's eye 60 while maintaining a constant positional relationship between the target 62a and the light source 62b.

Figure 2:
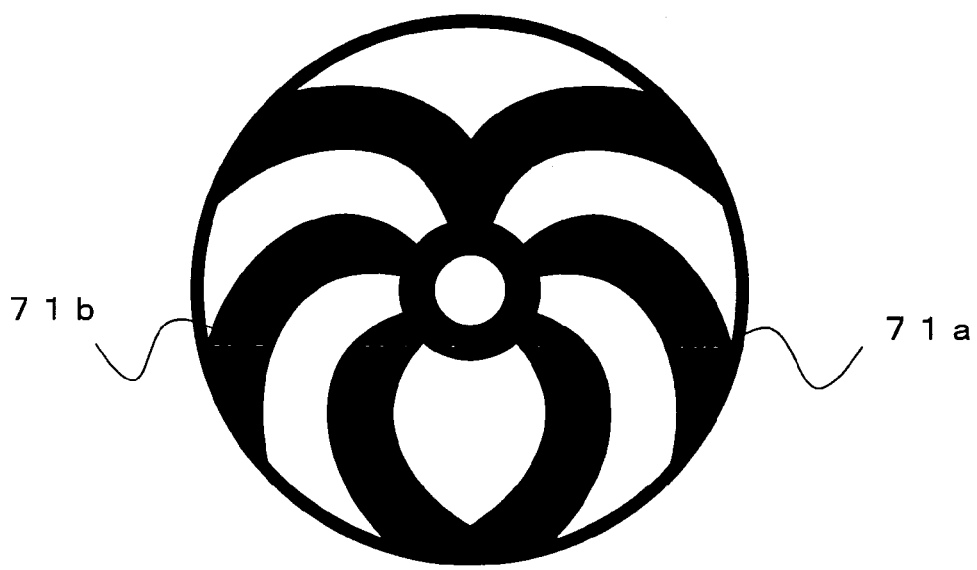

FIG. 2 is a diagram showing a striped pattern of a chopper 61a.

The refraction measurement section 61 includes the chopper 61a having slits formed therein, a motor 61i which rotates the chopper 61a, a light source (infrared light source) 61b which illuminates the chopper 61, a lens 61d which projects a striped pattern formed by the chopper 61a onto the fundus of the subject's eye 60, a light-receiving section 61h which detects the moving velocity of the striped pattern formed by light returned from the fundus of the subject's eye 60, a lens 61f, a diaphragm 61g, and the like. The refraction measurement section 61 also includes a lens 61c, a half mirror 61e, and the like.

The dichroic mirror 63 respectively guides measurement light (infrared light) emitted from the refraction measurement section 61 and measurement light (visible light) emitted from the projection section 62 to the subject's eye 60, and returns the infrared light from the subject's eye 60 to the refraction measurement section 61. In the refraction measurement section 61, the chopper 61a rotates so that the striped pattern projected onto the fundus of the subject's eye 60 moves. The moving velocity of the striped pattern formed on the light-receiving section 61h changes corresponding to the refractive power of the subject's eye 60. As shown in FIG. 2, stripes 71a and 71b in two directions are formed on the chopper 61a as the striped pattern. When the chopper has made a round, two meridional directions are measured so that the refractive power such as the spherical power, cylinder power, and astigmatic axis are calculated.

The control section 65 includes a CPU, a circuit including a memory used for the operation of the CPU, and the like. The control section 65 controls the operations of the light sources 62b and 61b, the motors 62e and 61i, and the display section 66 and performs a calculation by referring to signals output from the light-receiving section 61h. In more detail, the control section 65 disposes the target 62a (target 62a and light source 62b) and scans the position of the target 62a by referring to the output from the refraction measurement section 61 while driving the refraction measurement section 61 (controlling the operation of the motor 62d while driving the light source 62b).

The control section 65 determines the refractive power of the subject's eye 60 as described above by referring to the output from the light-receiving section 61h while driving the light source 61b, the motor 61i, and the light-receiving section 61h.

A method of causing the control section 65 to perform accommodation function state measurement by using the device having the above-described configuration is described below.

Figure 3:
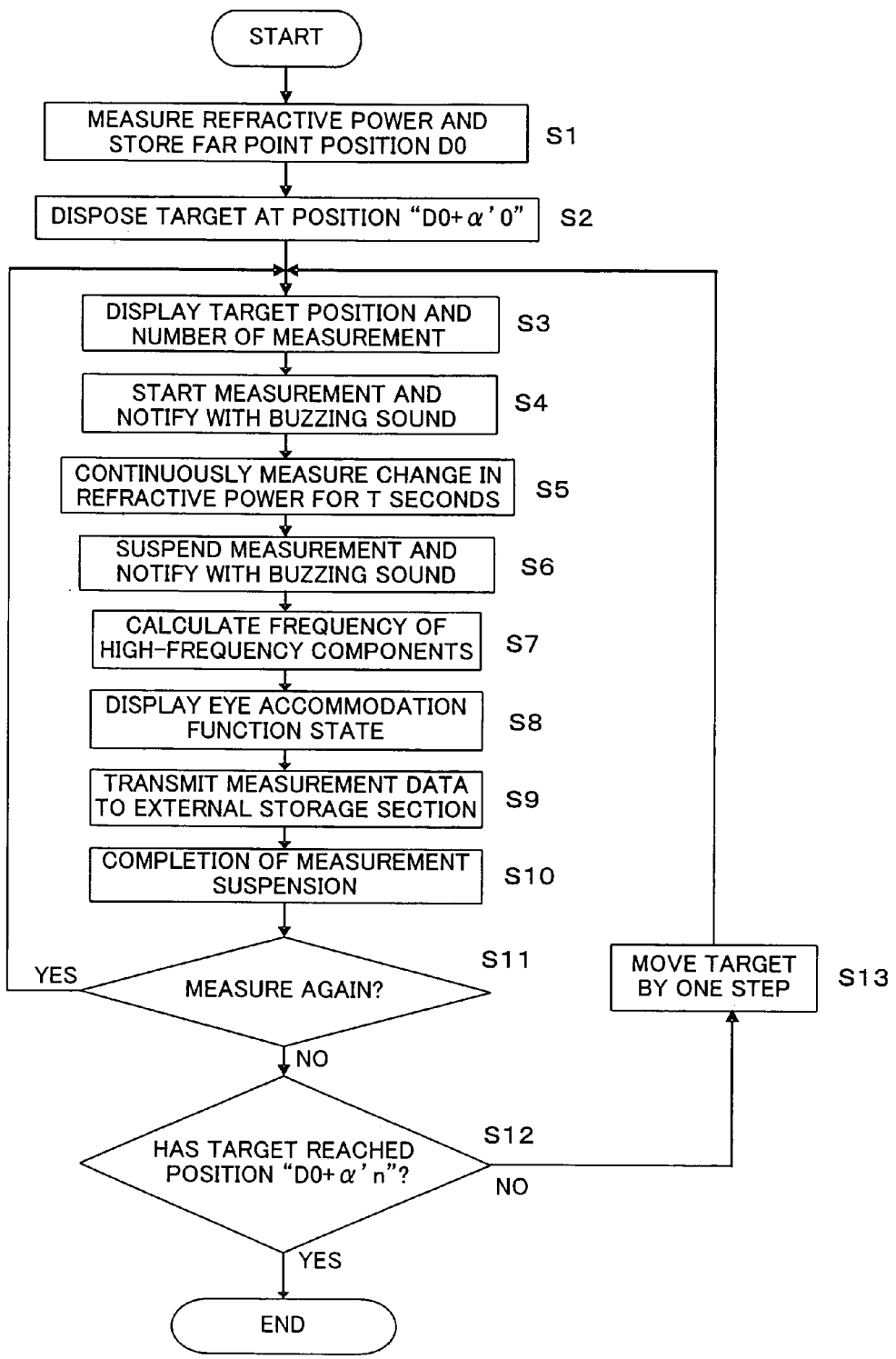
FIG. 3 is an operation flowchart of a control section 15.

FIG. 3 is an operation flowchart of the control section 15.

As preparation measurement before conducting main measurement, the far point position, which is one of the characteristics of the subject's eye 60, is measured. The far point position is the target position at which the subject's eye can see the farthest target, and is measured in order to adjust the main measurement procedure corresponding to the properties of the subject's eye 10. The far point position is measured in the same as in general refractive power measurement, and the measurement method is disclosed in the patent document 1. Therefore, details of the far point position measurement are omitted. After the measurement has been completed, a far point position D0 is stored in the memory (step 1: "step" is hereinafter abbreviated as "S").

In the subsequent main measurement procedure, a target 12*a* is disposed at a position "D0+a'0" a little farther than the far point position D0 (S2). The position "D0+a'0" is the position at which the subject's eye 60 cannot clearly see the target 62*a* even after accommodation but the target 62*a* is not blurred to a large extent. The target 62*a* is disposed at the position "D0+a'0" in order to prevent unnecessary movement of the subject's eye 60. Therefore, it is preferable that a'0 be about 0.5 Dp. The target position and the number of the measurement are displayed in the display section 66 (S3). This aims at allowing the operator and the subject to easily recognize the number of the current measurement, since the measurement after S3 is performed for eight cycles. The display section 66 displays the number of the current cycle and the number of remaining cycles.

Figure 4:
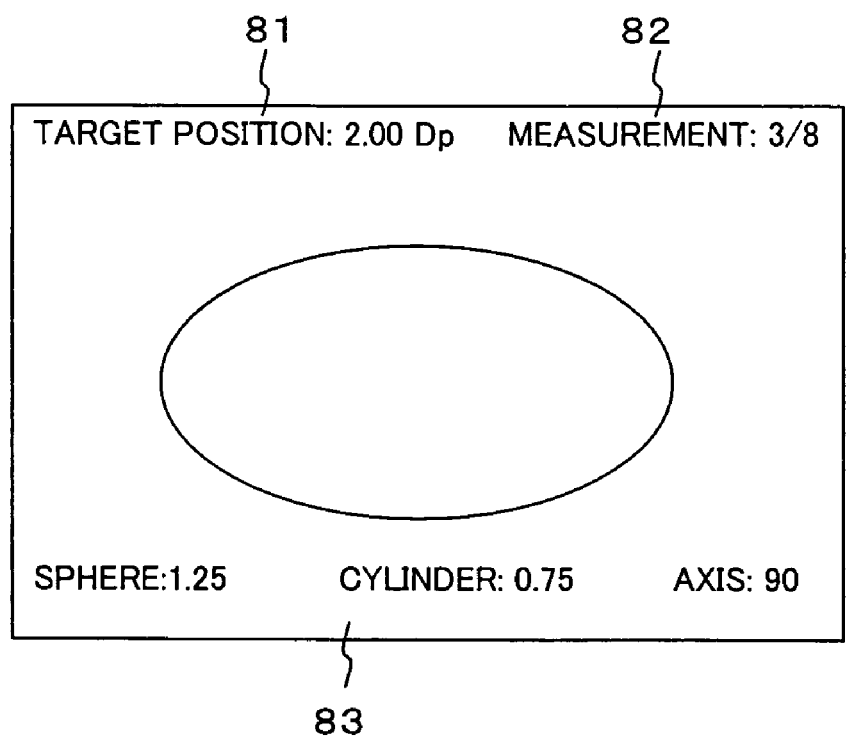
FIG. 4 is a diagram showing a display example in S3 shown in FIG. 3.

FIG. 4 is a diagram showing a display example in S3 shown in FIG. 3.

In one embodiment of the present invention, target position information 81 indicating the target position (indicating the position "2Dp" in FIG. 4) and measurement time information 82 indicating the number of the current cycle in the eight cycles (indicating that the current cycle is the third cycle of the eight cycles in FIG. 4) are displayed in addition to a refractive power measured value 83. Such indications are displayed for the operator and the subject as the measurement standard by using the display section 66 such as a liquid crystal screen or a CRT.

A measurement start buzzing sound is output from the sound output section 67 to indicate start of measurement to the subject (S4). A buzzing sound is unnecessary when the measurement time is short. However, since the main measurement time is as long as 20 seconds, a buzzing sound is output so that measurement preparation, such as prompting the subject to blink, can be performed.

The target 62*a* is continuously disposed at an idetical position for a specific time T, and a time-varying change in the refractive power is monitored (S5). The time T (period in which time-varying refractive power change data is sampled) is about eight seconds or more and about 20 seconds or less within which a burden on the ciliary muscle due to staring of the subject's eye 10 is small. The time T is set at about eight seconds or more because it is necessary to sample a sufficient amount of data in order to maintain the accuracy of calculation (S7) for determining the occurrence frequency of high-frequency components. In this device, the time T is set at 20 seconds.

When the measurement for 20 seconds has been completed, the subject is notified of the completion of measurement in one cycle by using a buzzing sound (operation as measurement suspension notification section), and the measurement is suspended (S6). Therefore, the subject can rest and ease strain.

An analysis procedure is then performed. The control section 65 calculates the frequency of high-frequency components from the measured values (S7). Since the measurement is performed at intervals of 0.1 second, the control section 65 fully operates during the measurement for calculating the measured values. However, since the control section 65 does not fully operate after the measurement has been suspended, the control section 65 can calculate the frequency of high-frequency components of the preceding eye accommodation function state measurement results by utilizing the measurement suspension period.

A result display procedure is then performed. When the calculation has been completed, the intermediate results of the eye accommodation function state measurement are displayed (S8).

Figure 5:
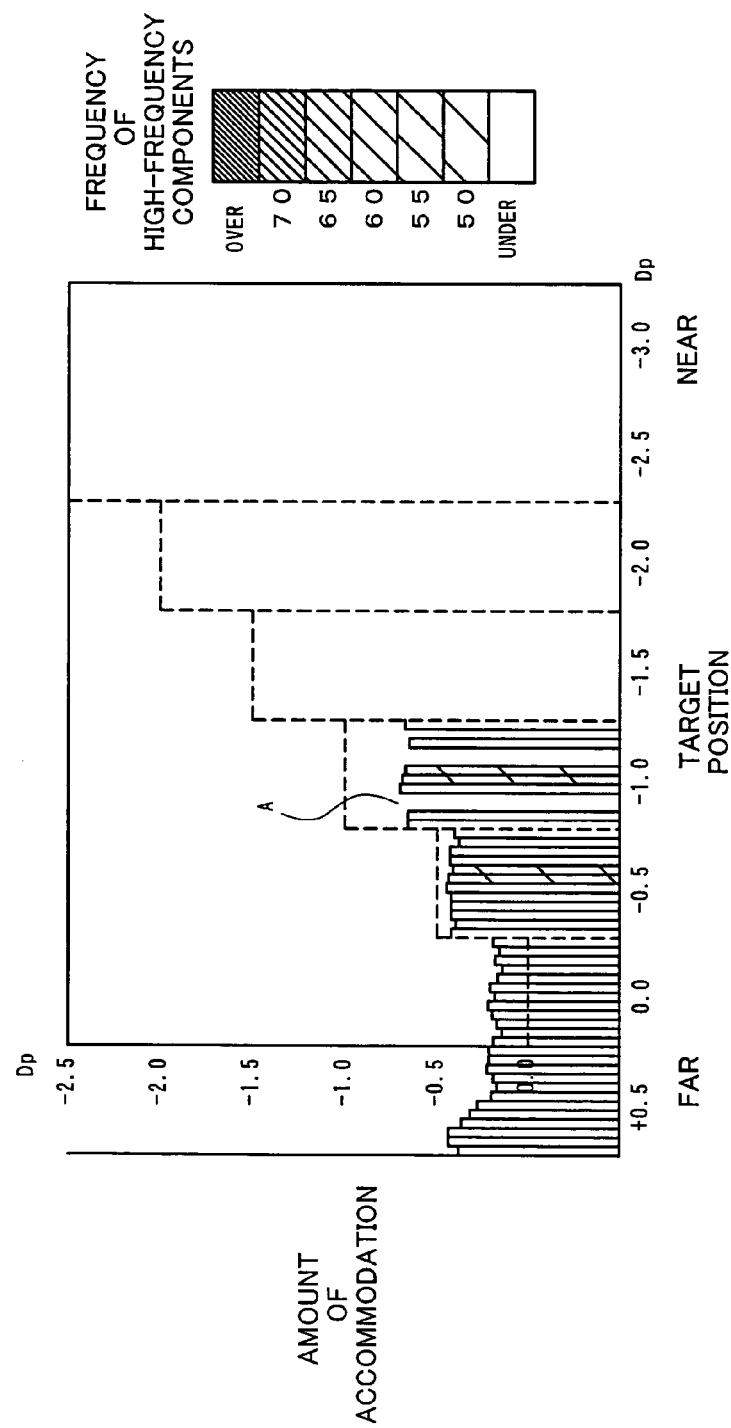
FIG. 5 is a diagram showing an intermediate result display example.

FIG. 5 is a diagram showing an intermediate result display example.

Figure 6:
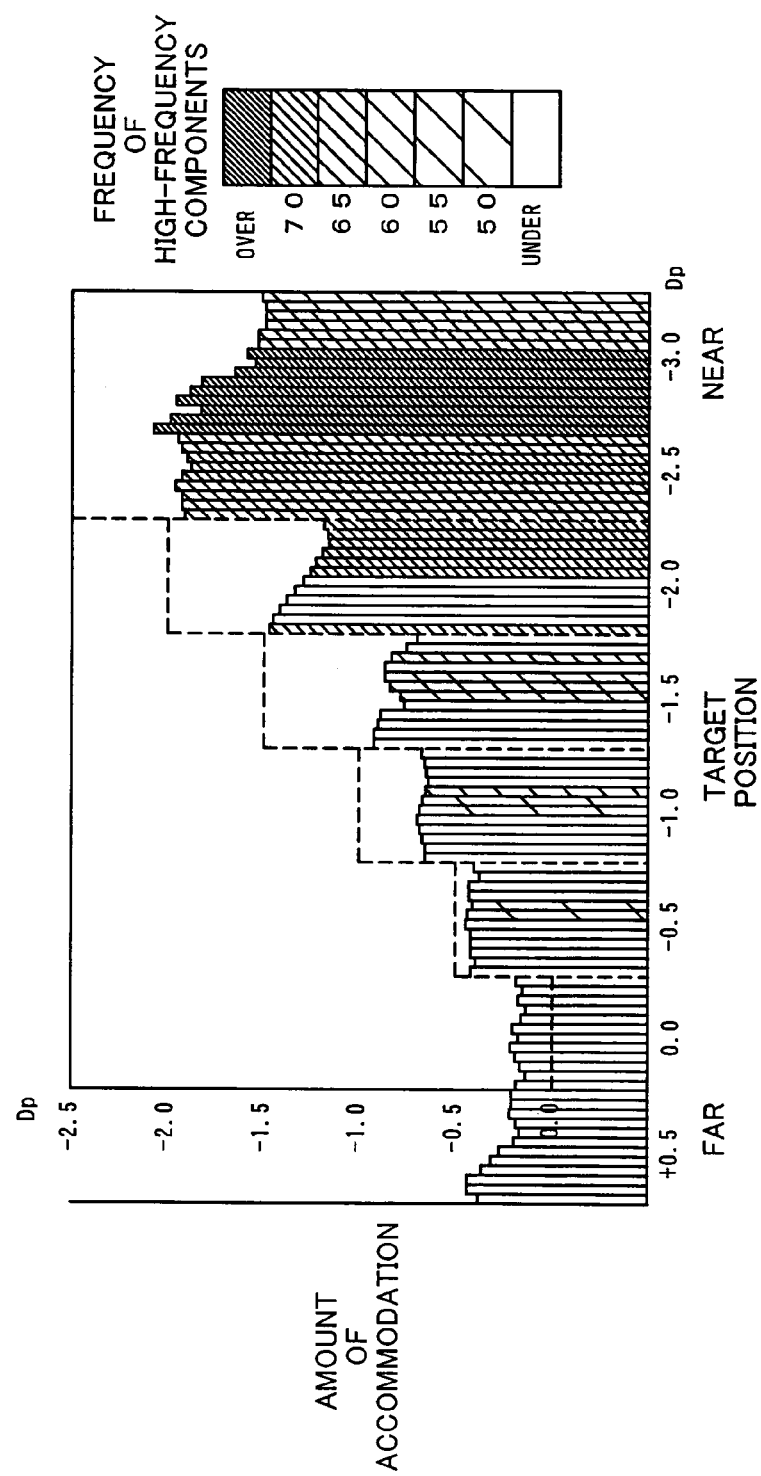
FIG. 6 shows measurement results after all the measurements have been completed.

FIG. 6 shows the measurement results after all the measurements have been completed.

FIGS. 5 and 6 show the occurrence frequency of high-frequency components at each target position a'i (i=0 to n) in interval units.

In the examples shown in FIGS. 5 and 6, the target position is indicated in interval units in the range of +0.5 Dp to −3.0 Dp. The accommodation state of the subject's eye is indicated by classifying the bar graph according to the occurrence frequency (expressed with hatching lines in FIGS. 5 and 6). The higher the frequency of high-frequency components, the darker the color, and the lower the frequency of high-frequency components, the lighter the color. Therefore, the accommodation state of the subject's eye can be known from the color or the depth of the color.

FIG. 5 shows an example in which the measurement has not been completed and is performed only up to a target position of −1.0. For example, a bar of the bar graph is omitted when a measurement error has occurred (as indicated by "A" in FIG. 5), so that it is possible to determine whether or not a measurement error has occurred.

Then, the data is transmitted from the control section 65 to the external storage section 69 (S9). Therefore, since it suffices that only the measurement data in one cycle be stored in the memory, the capacity of the storage section such as a memory provided in the device can be minimized, so that it is unnecessary to provide a large capacity memory. The measurement suspension is thus completed (S10).

Before moving the target by one step, the operator is asked whether or not to perform the measurement again without moving the target (S11). This aims at allowing remeasurement to be performed before moving the target when the operator has determined that remeasurement is necessary after seeing the display of the intermediate results (FIG. 5). When the operator has selected remeasurement (by using the remeasurement select section 68) ("YES" in S11), the measurement is performed again in S3. When the operator has selected to move the target without selecting remeasurement ("NO" in S11), the operation proceeds to S12.

The control section 65 determines whether or not the target position has reached "D0+a'n" (whether or not "n" has reached eight). If "NO", the control section 65 moves the target by one step (e.g. 0.5 Dp) (S13). Then, the measurement is performed in S3 in the same manner as described above. If "YES", all the measurements are stopped.

The calculation method for the frequency of high-frequency components and the display method for the eye accommodation function state are essentially the same as those described in the patent document 1. Therefore, description of these methods is omitted.

The present invention is not limited to the above-described embodiments, and various modifications and variations may be made. Such modifications and variations are also within the scope of equivalence of the present invention.

For example, the above-described embodiments illustrate an example in which the external storage section 69 is a dedicated device. However, the present invention is not limited thereto. A device including a CPU and a memory, such as a personal computer, may be used, for example. In this case, data may be transmitted in S9 before the control section 65 calculates the eye accommodation function state, and the personal computer may calculate the eye accommodation function state. The present invention aims at reducing the load imposed on the control section of the eye accommodation function state measurement device by performing calculation processing and data transmission within the measurement suspension period. Therefore, data transmission and calculation processing may be performed by using an arbitrary control section, and the order of data transmission and calculation processing may be reversed insofar as the data transmission and the calculation processing are performed within the measurement suspension period.

The invention claimed is:

1. An eye accommodation function state measurement device, comprising:
   an image projection section which projects an image onto a subject's eye;
   an image moving mechanism which moves a position of the image along a direction of an optical axis of the subject's eye; and
   a control section which provides a measurement suspension period in which the measurement is suspended, wherein
   the eye accommodation function state measurement device disposes the image at a plurality of positions by using the image moving mechanism, and measures an accommodation function state of the subject's eye at each position, and
   an intermediate measurement result of the eye accommodation function state is displayed within the measurement suspension period.

2. The eye accommodation function state measurement device according to claim 1, wherein the control section calculates the eye accommodation function state within the measurement suspension period.

3. The eye accommodation function state measurement device according to claim 1, further comprising a measurement suspension notification section which indicates start and/or completion of the measurement suspension by using a display and/or voice.

4. The eye accommodation function state measurement device according to claim 1, wherein the control section transmits data to an external storage section in the measurement suspension period.

5. An eye accommodation function state measurement device comprising:
   an image projection section which projects an image onto a subject's eye;
   an image moving mechanism which moves a position of the image along a direction of an optical axis of the subject's eye; and
   a control section which provides a measurement suspension period in which the measurement is suspended; and
   a remeasurement select section which allows selection of remeasurement without moving the position of the image in the measurement suspension period, wherein
   the eye accommodation function state measurement device disposes the image at a plurality of positions by using the image moving mechanism, and measures an accommodation function state of the subject's eye at each position.

6. An eye accommodation function state measurement device comprising: an image projection section which projects an image onto a subject's eye; and an image moving mechanism which moves a position of the image along a direction of an optical axis of the subject's eye; the eye accommodation function state measurement device disposing the image at a plurality of positions by using the image moving mechanism, measuring an accommodation function state of the subject's eye at each position, and displaying at least one of positional information of the image and measurement time information at least in the middle of the measurement.

* * * * *